United States Patent [19]

Holroyd

[11] Patent Number: 5,014,547

[45] Date of Patent: May 14, 1991

[54] APPARATUS FOR DETERMINING THE SURFACE ROUGHNESS OF A MATERIAL

[75] Inventor: Trevor J. Holroyd, Derby, England

[73] Assignee: Stresswave Technology Limited, Derby, England

[21] Appl. No.: 418,261

[22] Filed: Oct. 6, 1989

[30] Foreign Application Priority Data

Nov. 15, 1988 [GB] United Kingdom ................ 8826640

[51] Int. Cl.⁵ ...................... G01B 17/00; G01B 21/30; G01N 29/14

[52] U.S. Cl. ........................................ 73/105; 73/159; 73/587

[58] Field of Search ................ 73/105, 159, 7, 104, 73/649, 651, 652, 587

[56] References Cited

U.S. PATENT DOCUMENTS

| | | | |
|---|---|---|---|
| 2,752,781 | 7/1956 | Thorsen | 73/159 |
| 2,896,196 | 7/1959 | Hartford et al. | 73/159 X |
| 3,037,381 | 6/1962 | Grant et al. | 73/159 |
| 3,164,015 | 1/1965 | Schäfer | 73/159 |
| 4,448,062 | 5/1984 | Peterson et al. | 73/587 X |
| 4,538,463 | 9/1985 | Pease | 73/587 |
| 4,541,278 | 9/1985 | Marsh et al. | 73/105 X |
| 4,563,897 | 1/1986 | Moor | 73/587 |
| 4,819,994 | 4/1989 | Holroyd | 303/100 |

FOREIGN PATENT DOCUMENTS

| | | |
|---|---|---|
| 3020348 | 12/1981 | Fed. Rep. of Germany . |
| 973585 | 2/1951 | France ................ 73/105 |
| 2606152 | 5/1988 | France . |
| 94258 | 5/1985 | Japan .............. 73/587 |
| 61-198057 | 2/1986 | Japan . |
| 61-91566 | 9/1986 | Japan . |
| 73186 | 4/1987 | Japan .............. 73/587 |
| 1151815 | 4/1985 | U.S.S.R. .......... 73/105 |
| 1221585 | 3/1986 | U.S.S.R. .......... 73/587 |
| 1352207 | 11/1987 | U.S.S.R. .......... 73/105 |
| 1477006 | 6/1977 | United Kingdom . |
| 2042727 | 9/1980 | United Kingdom . |

Primary Examiner—Tom Noland
Attorney, Agent, or Firm—Cushman, Darby & Cushman

[57] ABSTRACT

An apparatus for determining the surface roughness of a material comprised of an acoustic element which is pivotally mounted to a support structure containing a polished end which is maneuvered into contact with the surface of a material to be tested by a spring element. The material is caused to move relative to the acoustic element by a driven roller. A transducer is acoustically coupled to the acoustic element and detects stress waves propagating in the acoustic element as a result of frictional and impact force generated by the rubbing of the acoustic element with the material. The relative stress wave activity is dependent upon the surface roughness of the material. A processor analyzes an electrical signal produced by the transducer to determine the surface roughness of the material which may analyze the electrical signal produced by the transducer to determine the presence of impurities on the surface of the material.

15 Claims, 2 Drawing Sheets

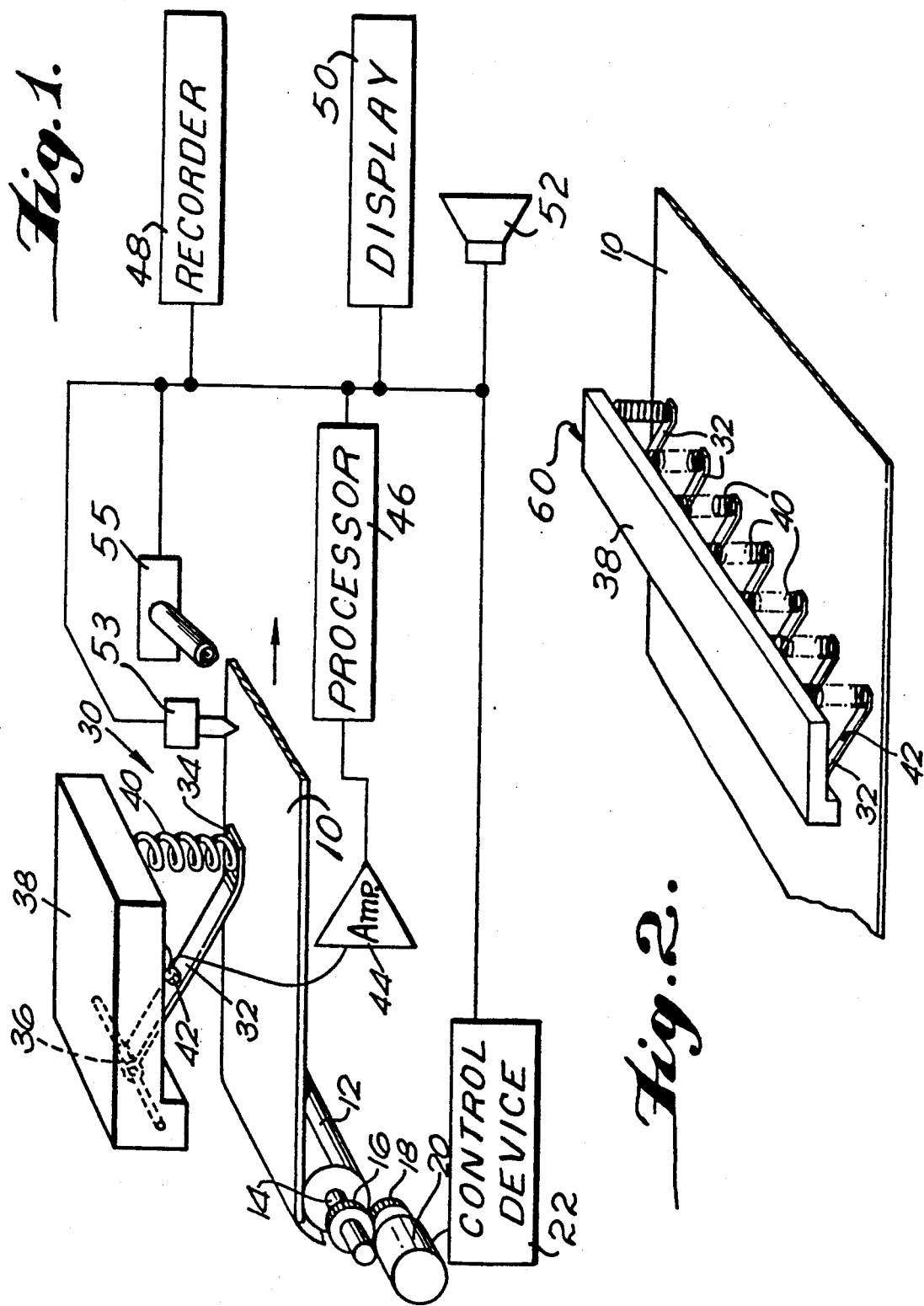

APPARATUS FOR DETERMINING THE SURFACE ROUGHNESS OF A MATERIAL

BACKGROUND OF THE INVENTION

The present invention relates to an apparatus for determining the surface roughness of a material.

A conventional method of determining the surface roughness of a material uses a probe which has a stylus. The probe is moved relative to the material and the stylus makes contact with and moves over the surface of the material. As the stylus moves over the surface of the material, displacements of the stylus are transferred directly as stresses or strains to a sensitive element in the probe. This method has several drawbacks such as the relative speed of movement between the stylus and the material must be sufficiently low so that surface irregularities may be resolved. Furthermore the stylus must have a fine point in order for it to ride up and down the surface irregularities, giving rise to the possibility of tearing relatively thin sheet materials. This principle of determining surface roughness requires a compromise to be made between sensitivity and ruggedness.

SUMMARY OF THE INVENTION

The present invention seeks to provide an apparatus for determining the surface roughness of a material which allows relatively high speed of relative movement between the apparatus and the material, and has a relatively large contact area with the material.

Accordingly the present invention provides an apparatus for determining the surface roughness of a material comprising at least one acoustic element arranged in contact with a surface of a material, means to cause relative movement between the at least one acoustic element and the material such that frictional contact between the at least one acoustic element and the material generates stress waves which propagate within the at least one acoustic element, the stress wave activity within the at least one acoustic element being dependent upon the surface roughness of the material, acoustic emission transducer means acoustically coupled to the at least one acoustic element arranged to detect stress waves propagating in the at least one acoustic element to produce at least one electrical signal, and means to determine from the at least one electrical signal the surface roughness of the material.

The at least one acoustic element may be biassed into contact with the surface of the material.

The at least one acoustic element may be biassed into contact with the surface of the material by spring means.

A plurality of acoustic elements may be arranged in contact with the surface of the material, the acoustic elements being spaced transversely of the material with respect to the direction of relative movement of the material and acoustic elements.

The acoustic elements may be equi-spaced.

The acoustic element may extend transversely of the material with respect to the direction of relative movement of the material and acoustic element, the acoustic element making contact with substantially the full width of the material.

The acoustic element may have a polished surface which makes contact with the material.

The acoustic element may have a relatively large surface area which makes contact with the surface of the material.

A single transducer may be acoustically coupled to each acoustic element.

The acoustic element may be rod shaped, the acoustic element may be rotated about its axis.

The acoustic element may be shaped and configured such that the stress waves propagating in the acoustic element have a relatively low decay rate at the frequency or frequencies being detected in order to create a diffuse stress wave field.

The material may be a thin sheet.

The material may be paper.

The material may be moved relative to the acoustic element.

The acoustic element may be pivotally mounted to a fixed structure.

The means to determine the surface roughness of the material may produce an output signal which operates an alarm when the surface roughness reaches a predetermined value.

The means to determine the surface roughness of the material may produce an output signal which controls the means to cause relative movement between the acoustic element and the material to at least reduce the relative movement when the surface roughness reaches a predetermined value.

The means to determine the surface roughness of the material may produce an output signal which operates a marker device when the surface roughness reaches a predetermined value, the marker device applies a mark onto the material.

The means to determine the surface roughness of the material may be adapted to determine the presence of impurities at the surface of the material.

The impurities may reduce the stress wave activity in the acoustic element.

The impurities may be oil or water.

The impurities may increase the stress wave activity in the acoustic element.

The impurity may be grit or scale.

The means to determine the surface roughness of the material may produce an output signal which operates a device to remove impurities when the surface roughness reaches a predetermined value.

BRIEF DESCRIPTION OF THE DRAWINGS

The present invention will be more fully described by way of example with reference to the accompanying drawings, in which:

FIG. 1 is a first embodiment of an apparatus for determining the surface roughness of a material or for determining the presence of impurities in the surface of a material.

FIG. 2 is a second embodiment of an apparatus for determining the surface roughness of a material or for determining the presence of impurities in the surface of a material.

DESCRIPTION OF THE PREFERRED EMBODIMENT

Figure 3:
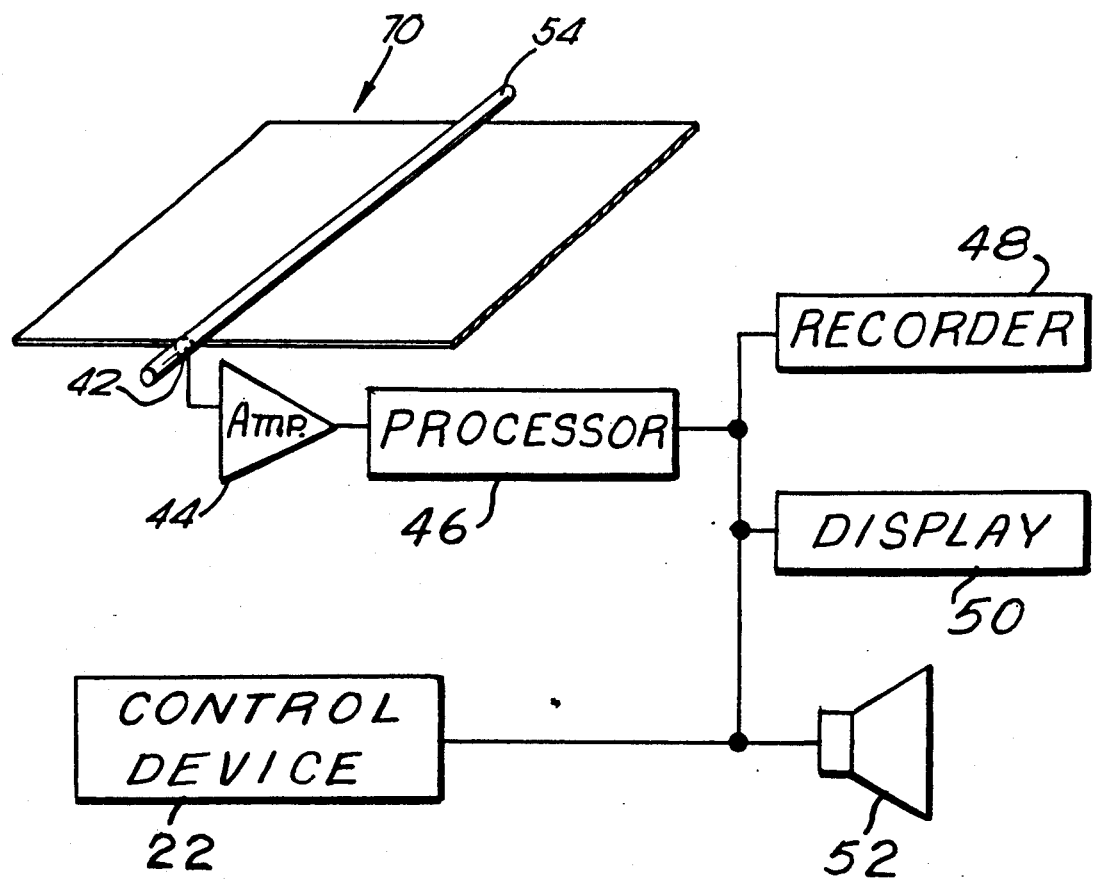
FIG. 3 is a third embodiment of an apparatus for determining the surface roughness of a material or for determining the presence of impurities in the surface of a material.

An apparatus 30 for determining the surface roughness of a material 10 is shown in FIG. 1. The apparatus 30 comprises an acoustic element 32 which is pivotally mounted at one end by a pivot 36 to a fixed support structure 38. The other end 34 of the acoustic element 32 has a controlled surface finish, for example the end 34 is polished, and preferably has a large surface area for frictional contact with the surface of the material 10.

A spring 40 is positioned between the support structure 38 and the end 34 of the acoustic element 32 to urge the end 34 of the acoustic element 32 into contact with the surface of the material 10. An acoustic emission type transducer 42 is acoustically coupled to the acoustic element 32 to detect any stress waves propagating in the acoustic element 32 and to convert the stress waves into an electrical signal. The acoustic emission transducer 42 is electrically connected in series to an amplifier 44 and processor 46. The processor 46 is electrically connected to a recorder 48, a display 50, an alarm 52 and a control device 22.

The material 10 is moved relative to the acoustic element 32 by a roller 12, the roller 12 is rotatably mounted by a spindle 14 upon a further support structure (not shown). The spindle 14 has a gear arrangement 16 which meshes with, and is driven by, a gear arrangement 18. The gear arrangement 18 is driven by an electric motor 20 which is operated by the control device 22.

In operation the material 10 is moved relative to the acoustic element 32 by the roller 12, and the acoustic element 32 is urged into contact with the surface of the moving material 10. The relative movement between the material 10 and the acoustic element 12 and the contact between the surface of the material 10 and the acoustic element 32 results in frictional and impact forces which generates broadband stress wave activity. The stress waves generated as a result of the frictional and impact forces propagate within the acoustic element 32. The acoustic emission transducer 42 detects the stress waves and converts them into an electrical signal. The electrical signal is amplified by the amplifier 44 and is then transmitted to the processor 46 which determines the surface roughness of the material from the electrical signal.

The processor 46 sends an output signal to the recorder 48 and the display 50. The processor 46 may also send an output signal to the alarm 52 or to the control device 22 when the surface roughness reaches a predetermined value. The control device may reduce or preferably stop the movement of the material 10.

The acoustic element is shaped and configured such that at the frequencies of interest the stress waves have a low decay rate to effectively trap the stress waves in the acoustic element for a short period of time to create a diffuse field. As a result the acoustic element provides an inherent averaging function for the stress wave activity both over the area of contact and as a function of time. The measurement of the stress wave activity in the acoustic element provides an integrated or mean indication of the surface roughness of the material. In view of the diffuse field of stress wave activity in the acoustic element it is only necessary to have a single acoustic emission transducer detecting the stress waves, and the transducer may be positioned at any arbitrary position on the acoustic element.

FIG. 2 shows an apparatus 60 for determining the surface roughness of a material 10, and which determines variations of surface roughness over the width of the material at a plurality of positions arranged transversely to the direction of movement of the material.

The apparatus 60 is substantially the same as the embodiment in FIG. 1 but comprises a plurality of acoustic elements 32 which are equi-spaced transversely to the direction of motion of the material 10. Each acoustic element 32 is pivotally mounted to the same support structure 38, or to independent support structures, and each acoustic element 32 is urged into contact with the material by a respective spring 40.

Each acoustic element 32 has an acoustic emission type transducer 42 acoustically coupled thereto, and each transducer 42 sends an electrical signal to a respective amplifier and processor.

FIG. 3 shows an apparatus 70 for determining the surface roughness of a material 10, and which produces an integrated measure over the width of the material transversely to the direction of movement of the material. The apparatus 70 comprises an acoustic element 54 of rod like or other elongated shape which makes contact with the surface of the material 10 over substantially the whole width of the material 10. An acoustic emission type transducer 42 is acoustically coupled to the acoustic element 54. The transducer 42 sends an electrical signal to an amplifier 44 and processor 46.

Although the description has referred to the use of springs to bias the acoustic element into contact with the surface of the material, other suitable forces may be used for example gravity, pneumatic, hydraulic or other pressure.

The invention is applicable for the determination of the surface roughness of materials such as paper or other thin sheet materials which are travelling at high speeds. The invention allows this determination to be carried out without tearing the material because of the relatively large area of contact between the acoustic element and the material.

It may be possible to arrange to move the acoustic element while the material remains stationary, or to move both.

For example the rod in FIG. 3 may be rotated about its axis while the material 10 remains static. The rod 54 may then be moved to a number of other locations along the material to determine the surface roughness, while the material remains static or alternatively the material may be moved relatively slowly while the rod 54 rotates.

The processor in the examples may also send an output signal to a marker device 53 which applies a mark onto the material at the appropriate position so as to enable identification of the portion of the material with a different surface roughness.

The apparatus as described with reference to the three figures is also applicable for the determination of the presence or absence of impurities or contaminants at the surface of a material which cause a change in the surface roughness of the material. The presence of contaminants on the surface of the material will either increase or decrease the normal level of the frictional and impact forces occurring during relative movement between the acoustic element and the material. This will either generate more or less stress waves than the normal level for the uncontaminated material.

The processor may be arranged to determine from the electrical signal, from the transducer, the presence of impurities at the surface of the material which cause a change in the surface roughness of the material. For example the presence of grit or scale would increase the stress wave activity compared to the normal stress wave level from the surface of paper, and the presence of a water, oil or other fluid would decrease the stress wave level.

The processor may be arranged to produce an output signal which operates a device 55 to remove impurities from the surface of the material when the stress wave activity in the acoustic element reaches a predetermined value. The predetermined value may be greater or less than the normal stress wave level depending on the type of impurity.

The term surface roughness of a material is intended to mean the irregularities of shape present at the surface of a material and the irregularities of shape present at the surface of a material produced by impurities at the surface of the material.

I claim:

1. An apparatus for determining the surface roughness of a material comprising at least one acoustic element arranged in contact with a surface of the material, means to cause relative movement between the at least one acoustic element and the material such that frictional contact between the at least one acoustic element and the material generates stress waves which propagate within the at least one acoustic element, the stress wave activity within the acoustic element being dependent upon the surface roughness of the material, acoustic emission transducer means acoustically coupled to the at least one acoustic element arranged to detect stress waves propagating in the at least one acoustic element and to produce at least one electrical signal, and means to determine from the at least one electrical signal the surface roughness of the material, said acoustic element being shaped and configured such that the stress waves propagating in the acoustic element have a relatively low decay rate at the frequency or frequencies being detected in order to create a diffuse stress wave field.

2. An apparatus as claimed in claim 1 in which the at least one acoustic element is biassed into contact with the surface of the material.

3. An apparatus as claimed in claim 1 in which a plurality of acoustic elements are arranged in contact with the surface of the material, the acoustic elements being spaced transversely of the material with respect to the direction of relative movement of the material and acoustic elements.

4. An apparatus as claimed in claim 3 in which the acoustic elements are equi-spaced.

5. An apparatus as claimed in claim 1 in which the acoustic element extends transversely of the material with respect to the direction of relative movement of the material and acoustic element, the acoustic element making contact with substantially the full width of the material.

6. An apparatus as claimed in claim 5 in which the acoustic element is rotated about an axis thereof.

7. An apparatus as claimed in claim 1 in which a single transducer is acoustically coupled to each acoustic element.

8. An apparatus as claimed in claim 1 in which the material is a thin sheet.

9. An apparatus as claimed in claim 1 in which the material is moved relative to the acoustic element.

10. An apparatus as claimed in claim 9 in which the acoustic element is pivotally mounted to a support structure.

11. An apparatus as claimed in claim 1 in which the means to determine the surface roughness of the material produces an output signal which operates an alarm when the surface roughness reaches a predetermined value.

12. An apparatus as claimed in claim 1 in which the means to determine the surface roughness of the material produces an output signal which operates a marker device when the surface roughness reaches a predetermined value, the marker device applies a mark onto the material.

13. An apparatus as claimed in claim 1 in which the means to determine the surface roughness of the material is arranged to determine the presence of impurities at the surface of the material.

14. An apparatus for determining the surface roughness of a material comprising at least one acoustic element arranged in contact with a surface of the material, means to cause relative movement between the at least one acoustic element and the material such that frictional contact between the at least one acoustic element and the material generates stress waves which propagate within the at least one acoustic element, the stress wave activity within the acoustic element being dependent upon the surface roughness of the material, acoustic emission transducer means acoustically coupled to the at least one acoustic element arranged to detect stress waves propagating in the at least one acoustic element and to produce at least one electrical signal, and means to determine from the at least one electrical signal the surface roughness of the material, said means to determine the surface roughness of the material producing an output signal which controls the means to cause relative movement between the acoustic element and the material to at least reduce the relative movement when the surface roughness reaches a pre-determined value.

15. An apparatus for determining the surface roughness of a material comprising at least one acoustic element arranged in contact with a surface of the material, means to cause relative movement between the at least one acoustic element and the material such that frictional contact between the at least one acoustic element and the material generates stress waves which propagate within the at least one acoustic element, the stress wave activity within the acoustic element being dependent upon the surface roughness of the material, acoustic emission transducer means acoustically coupled to the at least one acoustic element arranged to detect stress waves propagating in the at least one acoustic element and to produce at least one electrical signal, and means to determine from the at least one electrical signal the surface roughness of the material, said means to determine the surface roughness of the material being arranged to determine the presence of impurities at the surface of the material, and which operates a device to remove impurities when the surface roughness reaches a predetermined value.

* * * * *